United States Patent
Schaible et al.

(10) Patent No.: US 9,033,998 B1
(45) Date of Patent: May 19, 2015

(54) INDEPENDENT ROLL WRIST MECHANISM

(75) Inventors: Uwe Schaible, Ancaster (CA); Jeffrey Allan Veltri, Burlington (CA); Amin Ahmadi Bidhendi, Mississauga (CA); Reiza Rayman, Toronto (CA); Alexander Shvartsberg, Oakville (CA)

(73) Assignee: Titan Medical Inc., Toronto (CA)

( * ) Notice: Subject to any disclaimer, the term of this patent is extended or adjusted under 35 U.S.C. 154(b) by 268 days.

(21) Appl. No.: 13/106,306

(22) Filed: May 12, 2011

Related U.S. Application Data

(60) Provisional application No. 61/395,481, filed on May 13, 2010.

(51) Int. Cl.
*A61B 19/00* (2006.01)
*A61B 17/00* (2006.01)

(52) U.S. Cl.
CPC ... *A61B 17/00234* (2013.01); *A61B 2019/2234* (2013.01); *A61B 2017/003* (2013.01); *A61B 2017/00314* (2013.01); *A61B 2019/2238* (2013.01)

(58) Field of Classification Search
CPC .................. A61B 17/00234; A61B 2017/0138; A61B 2017/0147; A61B 2017/0161; A61B 2017/0175; A61B 2017/00314; A61B 2017/00327; A61B 2019/2223; A61B 2019/2234; A61B 2019/2238; A61B 2019/2242; A61B 2019/2246
USPC .......... 606/130, 205–208; 901/19, 21, 28, 30; 294/104, 209–210
See application file for complete search history.

(56) References Cited

U.S. PATENT DOCUMENTS

| | | |
|---|---|---|
| 4,068,156 A | 1/1978 | Johnson et al. |
| 4,149,278 A | 4/1979 | Wiker et al. |
| 4,283,165 A | 8/1981 | Vertut |
| 4,370,091 A | 1/1983 | Gagliardi |
| 4,511,305 A | 4/1985 | Kawai et al. |
| 4,626,165 A | 12/1986 | Nakashima et al. |
| 4,913,617 A | 4/1990 | Nicholson |
| 4,943,296 A | 7/1990 | Funakubo et al. |
| 5,178,032 A | 1/1993 | Zona et al. |
| 5,282,806 A * | 2/1994 | Haber et al. ................. 606/139 |
| 5,289,963 A | 3/1994 | McGarry et al. |
| 5,305,653 A | 4/1994 | Ohtani et al. |
| 5,374,277 A | 12/1994 | Hassler |
| 5,405,360 A | 4/1995 | Tovey |
| 5,785,647 A | 7/1998 | Tompkins et al. |
| 6,312,435 B1 | 11/2001 | Wallace et al. |
| 6,676,684 B1 | 1/2004 | Morley et al. |
| 6,817,974 B2 | 11/2004 | Cooper et al. |
| 6,902,560 B1 | 6/2005 | Morley et al. |

(Continued)

*Primary Examiner* — David Eastwood
*Assistant Examiner* — Martin T Ton
(74) *Attorney, Agent, or Firm* — Perry + Currier Inc.; Dolly Kao

(57) ABSTRACT

A robotic system for use in Minimally Invasive Surgery (MIS) is provided that, in various aspects of this specification, comprises at least one elongated shaft known as the robotic arm. In certain aspects, the robotic arm is provided with an independent roll wrist mechanism, which can allow for imparting the roll motion to the end effectors while mitigating or potentially eliminating the need of rotating the entire robotic arm, thus ensuring independent movement of end effectors. The independent movement of the end effectors sweeps a considerably smaller conical volume, as compared to that swept by the entire robotic arm, thereby reducing the likelihood of collisions with neighboring tissues or organs.

7 Claims, 15 Drawing Sheets

(56) References Cited

U.S. PATENT DOCUMENTS

| | | |
|---|---|---|
| 7,169,141 B2 | 1/2007 | Brock et al. |
| 7,214,230 B2 | 5/2007 | Brock et al. |
| 7,320,700 B2 | 1/2008 | Cooper et al. |
| 7,331,967 B2 | 2/2008 | Lee et al. |
| 7,371,210 B2 | 5/2008 | Brock et al. |
| 7,608,083 B2 | 10/2009 | Lee et al. |
| 7,637,905 B2 | 12/2009 | Saadat et al. |
| 7,699,835 B2 | 4/2010 | Lee et al. |
| 7,785,252 B2 | 8/2010 | Danitz et al. |
| 2002/0111621 A1 | 8/2002 | Wallace et al. |
| 2002/0177843 A1 | 11/2002 | Anderson et al. |
| 2002/0188293 A1 | 12/2002 | Manzo |
| 2003/0056561 A1 | 3/2003 | Butscher et al. |
| 2003/0060927 A1 | 3/2003 | Gerbi et al. |
| 2003/0135204 A1* | 7/2003 | Lee et al. .................. 606/1 |
| 2004/0167515 A1 | 8/2004 | Petersen et al. |
| 2004/0176751 A1 | 9/2004 | Weitzner et al. |
| 2005/0059960 A1 | 3/2005 | Simaan et al. |
| 2005/0251110 A1 | 11/2005 | Nixon |
| 2006/0074406 A1 | 4/2006 | Cooper et al. |
| 2007/0013336 A1 | 1/2007 | Nowlin et al. |
| 2007/0144298 A1 | 6/2007 | Miller |
| 2007/0173788 A1 | 7/2007 | Schena |
| 2007/0239028 A1 | 10/2007 | Houser et al. |
| 2007/0255109 A1 | 11/2007 | Stein et al. |
| 2008/0058776 A1 | 3/2008 | Jo et al. |
| 2008/0065102 A1* | 3/2008 | Cooper ...................... 606/130 |
| 2008/0065108 A1 | 3/2008 | Diolaiti |
| 2008/0163603 A1* | 7/2008 | Zubiate et al. ................ 59/84 |
| 2008/0255420 A1 | 10/2008 | Lee et al. |
| 2008/0294191 A1 | 11/2008 | Lee |
| 2008/0300462 A1* | 12/2008 | Intoccia et al. ............. 600/146 |
| 2009/0024141 A1* | 1/2009 | Stahler et al. ............... 606/130 |
| 2009/0171374 A1* | 7/2009 | Omori ........................ 606/130 |
| 2010/0331856 A1 | 12/2010 | Carlson et al. |
| 2011/0230894 A1 | 9/2011 | Simaan et al. |

* cited by examiner

INDEPENDENT ROLL WRIST MECHANISM

RELATED APPLICATIONS

The present specification claims priority from U.S. Provisional Patent Application 61/395,481 filed May 13, 2010, the contents of which are incorporated herein by reference.

FIELD

The present specification relates generally to robotic instruments, and more particularly, to a wrist mechanism of a robotic system for use in surgery.

BACKGROUND

With the gradual transition of surgical methods from the conventional process of making a long incision in a patient's body for performing a surgery to the next generation of surgery, i.e. minimally invasive surgery (MIS), continuous research is going on to develop and integrate robotic instruments in a system which can be used for MIS purposes. Such integration can help a surgeon to perform a surgery in an error-free manner, and at the same time to work in a realistic environment that gives the surgeon a feel of conventional surgery.

SUMMARY

An aspect of this specification provides a robotic surgical system comprising: an end-effector assembly comprising a surgical instrument configured for fine-movement responsive to a first control mechanism in order to perform a medical procedure at a target area using the surgical instrument; a coarse-movement assembly connected to the end-effector assembly; the coarse-movement assembly configured for coarse-movement responsive to a second control mechanism in order to position the end-effector assembly near the target area; the coarse-movement comprising at least a wrist movement for the end-effector assembly; the first control mechanism and the second control mechanism being independently controllable from each other.

The surgical instrument can comprise at least one of a clamp, a spatula, and surgical scissors.

The fine-movement can comprise movement in at least two axes.

The coarse-movement can comprise at least one of linear and rotational movement along at least one of the axes.

The coarse-movement can comprise movement in at least two axes along at least one of the axes.

The coarse-movement can comprise at least one of linear and rotational movement.

The coarse-movement can comprise an articulating joint assembly configured for linear movement along an X-axis. The articulating joint assembly can comprise a series of connected disks each independently moveable along the X-axis. The disks can each comprise at least one cavity for receiving at least one control cable implementing the first control mechanism.

The coarse-movement can comprise an articulating joint assembly configured for linear movement along an Y-axis. The articulating joint assembly can comprise a series of connected disks each independently moveable along the Y-axis. The disks can each comprise at least one cavity for receiving at least one control cable implementing the first control mechanism.

The coarse-movement can comprise a rotational assembly for providing roll.

The coarse-movement can comprise a first articulating joint assembly configured for linear movement along a first axis and a second articulating joint assembly configured for linear movement along a second axis perpendicular to the first axis. The first articulating joint assembly comprises a series of connected disks each independently moveable along the first axis; and the second articulating joint assembly comprises a series of connected disks each independently moveable along the second axis; the first articulating joint assembly being disposed at about ninety degrees in relation to the second articulating joint assembly.

The coarse-movement can comprise a rotational assembly for providing roll by rotating the coarse-movement assembly about a third axis perpendicular to both the first axis and the second axis.

Another aspect of this specification provides a robotic surgical system comprising: an end-effector assembly comprising a surgical instrument configured for fine-movement responsive to a first control mechanism in order to perform a medical procedure at a target area using the surgical instrument; a coarse-movement assembly connected to the end-effector assembly; the coarse-movement assembly configured for coarse-movement responsive to a second control mechanism in order to position the end-effector assembly near the target area; the first control mechanism and the second control mechanism being independently controllable from each other; the coarse-movement further comprising a first articulating joint assembly configured for linear movement along an X-axis and a second articulating joint assembly configured for linear movement along an Y-axis; the first articulating joint assembly comprising a series of connected disks each independently moveable along the X-axis; the second articulating joint assembly comprises a series of connected disks each independently moveable along the Y-axis; the first articulating joint assembly being disposed at about ninety degrees in relation to the second articulating joint assembly; the coarse-movement further comprising a rotational assembly for providing roll by rotating the coarse-movement assembly about the Z-axis.

BRIEF DESCRIPTION OF THE DRAWINGS

Various embodiments will now be described in which.

DETAILED DESCRIPTION OF THE EMBODIMENTS

Figure 1:
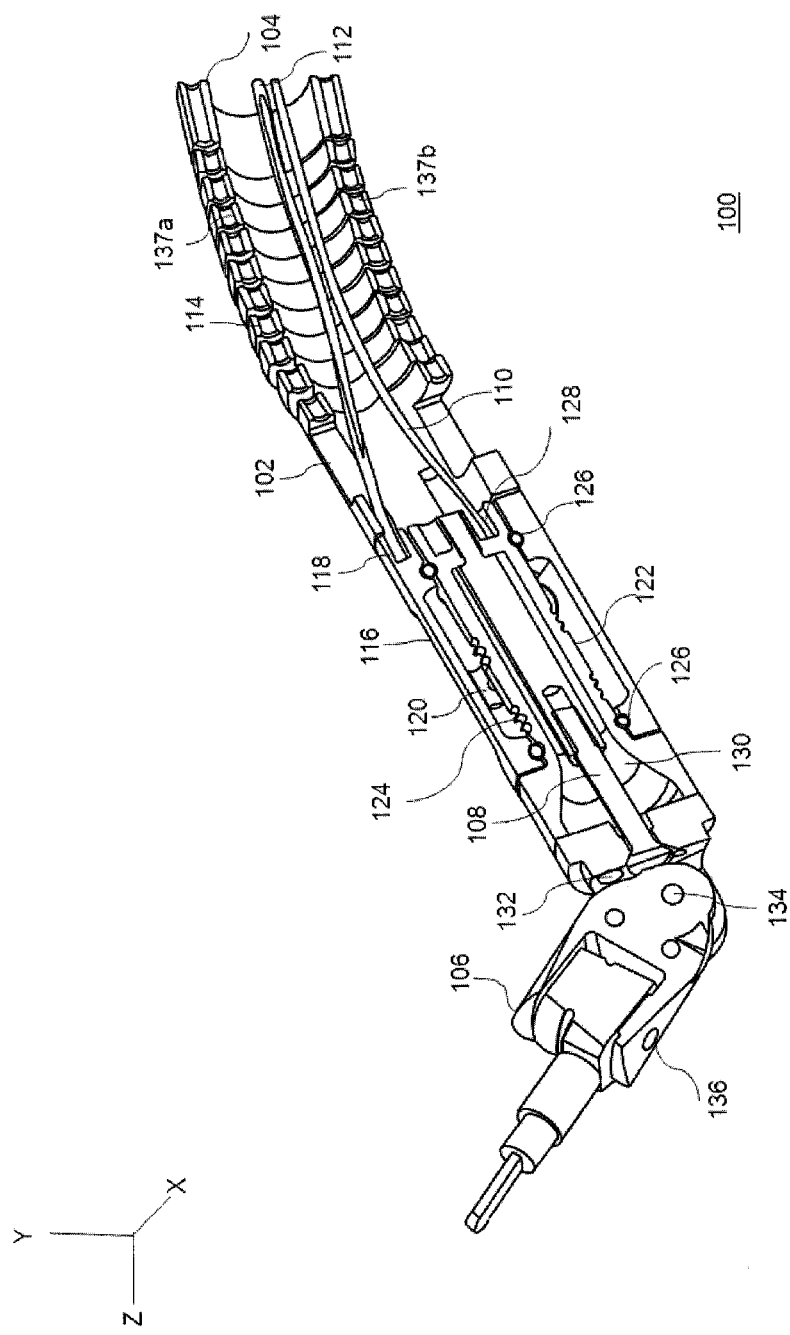
FIG. 1 illustrates a sectional view of a robotic system, in accordance with an embodiment of the present specification.

Minimally invasive surgery (MIS) can be performed by making small incisions, in the range of about 1-3 cm, in the patient's body and using pencil-sized instruments for performing the surgery. Most of the available robotic instruments used for MIS include one or more straight, elongated shafts, hereinafter referred to as robotic arms, which enter into the patient's body through the small incisions. At their one end, the robotic arms can carry imaging equipment, such as a camera, as well as pencil-sized surgical instruments, such as forceps and scissors. The pencil-sized surgical instruments and the imaging equipment can be collectively known as end effectors. These end effectors are rotated or moved inside the patient's body to perform the surgery. The end effectors are usually capable of roll, pitch and yaw motions. For the purpose of this description, the rotational motion of the end effectors about the axes X, Y and Z of the coordinate system (as shown in FIG. 1) are classified as pitch motion, yaw motion and roll motion respectively. The end effectors can also undergo movements that are a combination of those mentioned above.

In an embodiment of the present specification, a robotic system for use in MIS is described that comprises at least one elongated shaft known as the robotic arm. In this embodiment, an articulating joint assembly is attached at the proximal end i.e. the end closer to the patient, of the robotic arm. Further, end effectors are connected at the proximal end of the articulating joint assembly. The robotic arm is operatively connected to a console that is worked upon by a surgeon to control the movement of the end effectors through the robotic arm and the articulating joint assembly.

The robotic arm of the present specification is provided with an independent roll wrist mechanism. The independent roll wrist mechanism allows for imparting a roll motion to the end effectors without the need of rotating the entire robotic arm, thus ensuring independent movement of end effectors. The independent movement of the end effectors sweeps a considerably smaller conical volume, as compared to that swept by the entire robotic arm, thereby avoiding collisions with neighboring tissues or organs. The end effectors are capable of 180 degrees roll, both in clockwise and anti-clockwise direction. In addition, the system contemplates, according to the type of end effector selected, provisions for the conventional pitch, yaw and gripping motions of the end effectors.

FIG. 1 illustrates an arrangement 100 comprising mechanisms for imparting roll, pitch and yaw motions to the end effectors, according to one embodiment. The rotational motion of the end effectors about the axes X, Y and Z of the coordinate system, as shown in FIG. 1, are classified as pitch motion, yaw motion and roll motion respectively. The arrangement 100 can be a part of the robotic system described above. The arrangement 100 comprises an articulating joint assembly 102 connected to the robotic arm (not shown) at 104. An end effector assembly 106 is shown to be connected to the free end of the articulating joint assembly 102. In an embodiment, this connection can be realized by means of a retaining screw 108. The arrangement 100 comprises cables to control the pitch, yaw and roll motions of the end effector assembly 106. In the present embodiment, each cable can be paired with a counter-acting cable, and, in a present embodiment there is at least one cable pair to control each type of motion. The cable pairs can be actuated to impart the desired motion using various actuating means known in the art. In an embodiment, cable pairs are actuated using linear motors (not shown). In the embodiment shown in FIG. 1, three pairs of end cables such as 110 are present to control the pitch and yaw motions of the end effector assembly 106. Further, one pair of roll cables such as 112 is present to control the roll motion of the end effector assembly 106. In an embodiment, at least one cable pair (not shown) is also provided to control the motion of the articulating joint assembly 102 independently of the end effectors. Each cable of such a cable pair passes through the slots 137a and 137b provided at the circumference of each of the plurality of disks, such as disk 114. The plurality of disks (represented by the disk 114) together with a roll drum 122 form the articulating joint assembly 102.

The roll cables are guided along the articulating joint assembly 102 through the plurality of disks (represented by the disk 114) and enter a roll drum housing 116 at two entry points such as 118. Each cable is deflected by about ninety degrees by a roll cable-deflecting pulley 120 to wrap around the roll drum 122. The cable is wound around the drum on cable grooves such as 124, appropriately cut into the drum. The drum 122 is held inside the drum housing 116 through a bearing system 126 at either end of the housing 116. Hence, when the roll cable pair is actuated by the linear motors, it transmits the motion through the roll drums to the end effector assembly 106 and causes it to roll.

Similarly, the end cables 110 are guided by conduits through the disks 114 up to the drum rear-end at 128. The conduits are terminated at 128 and the end cables 110 are routed through the end-cable cavity 130 to the end-cable outlet 132 to impart pitch or yaw motions to the end effector assembly 106. Exemplary positions of the pitch pivot 134 and yaw pivot 136 have also been shown in FIG. 1.

Figure 2:
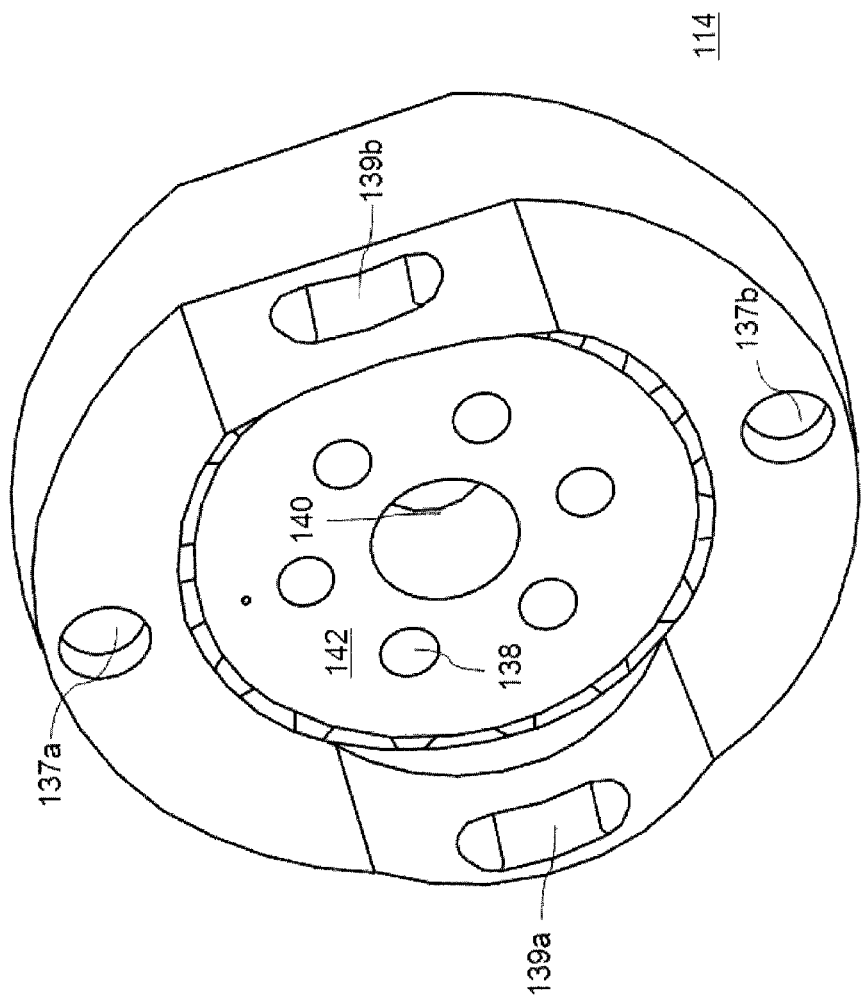
FIG. 2 illustrates a perspective view of a disk element used in the robotic system, in accordance with an embodiment of the present specification.

FIG. 2 shows a perspective view of the disk 114 according to an embodiment of the present specification. A plurality of disks similar to the disk 114 are joined together to form the articulating joint assembly 102 as shown in FIG. 1. Preferably, each of the plurality of disks comprises slots such as 138 and 140 through which the end cables and the roll cables pass. Preferably, these slots are formed on the periphery as well as on the central part of each of the plurality of disks. For the embodiment shown in FIG. 2, six slots similar to the slot 138 have been shown. Also, the disk 114 comprises slots 137a and 137b, as described above, for accommodating a cable pair that moves the articulating joint assembly. The central part 142 of the disk 114 is called the core. The disk 114 is also shown to have cavities 139a and 139b which receive attachment means such as bellows etc. for attaching the disk 114 to a subsequent disk in the articulating joint assembly. The plurality of disks together provides a passage for the roll cables and end cables through the articulating joint assembly 102.

Figure 3:
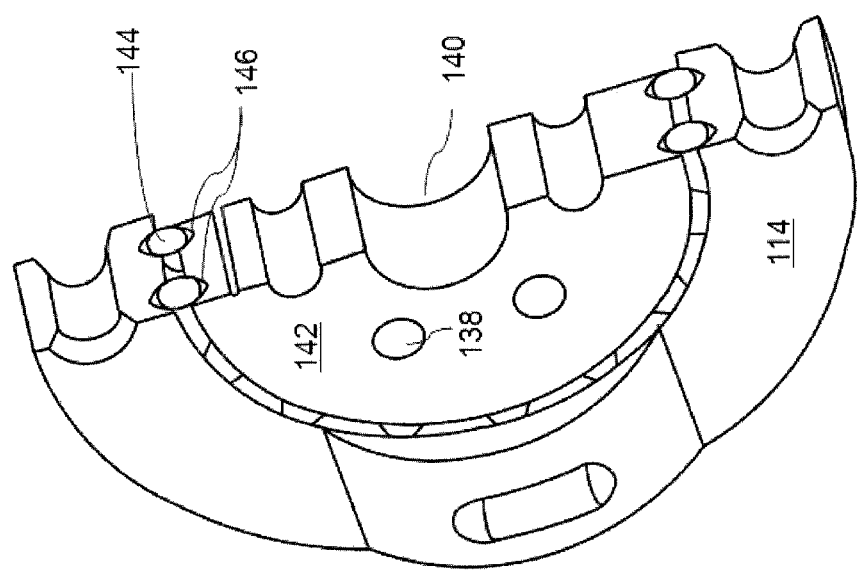
FIG. 3 illustrates a sectional view of the disk element, in accordance with an embodiment of the present specification.

FIG. 3 illustrates a sectional view of the disk 114. As described above, the disk 114 comprises a core 142. In an embodiment, the core 142 can rotate freely inside the disk 114. In this embodiment, the core 142 is secured inside the disk 114 by a bearing system. The bearing system is shown to comprise ball bearings 144 and a bearing race 146. The bearing race 146 is machined along the circumference of the core 142 and the ball bearings 144 travel on the bearing race 146. In this embodiment, the slot 140 provides a passage for the roll cables, whereas slots represented by 138 serve as passage for end-cables. These slots are as described above with reference to FIG. 2.

Figure 4:
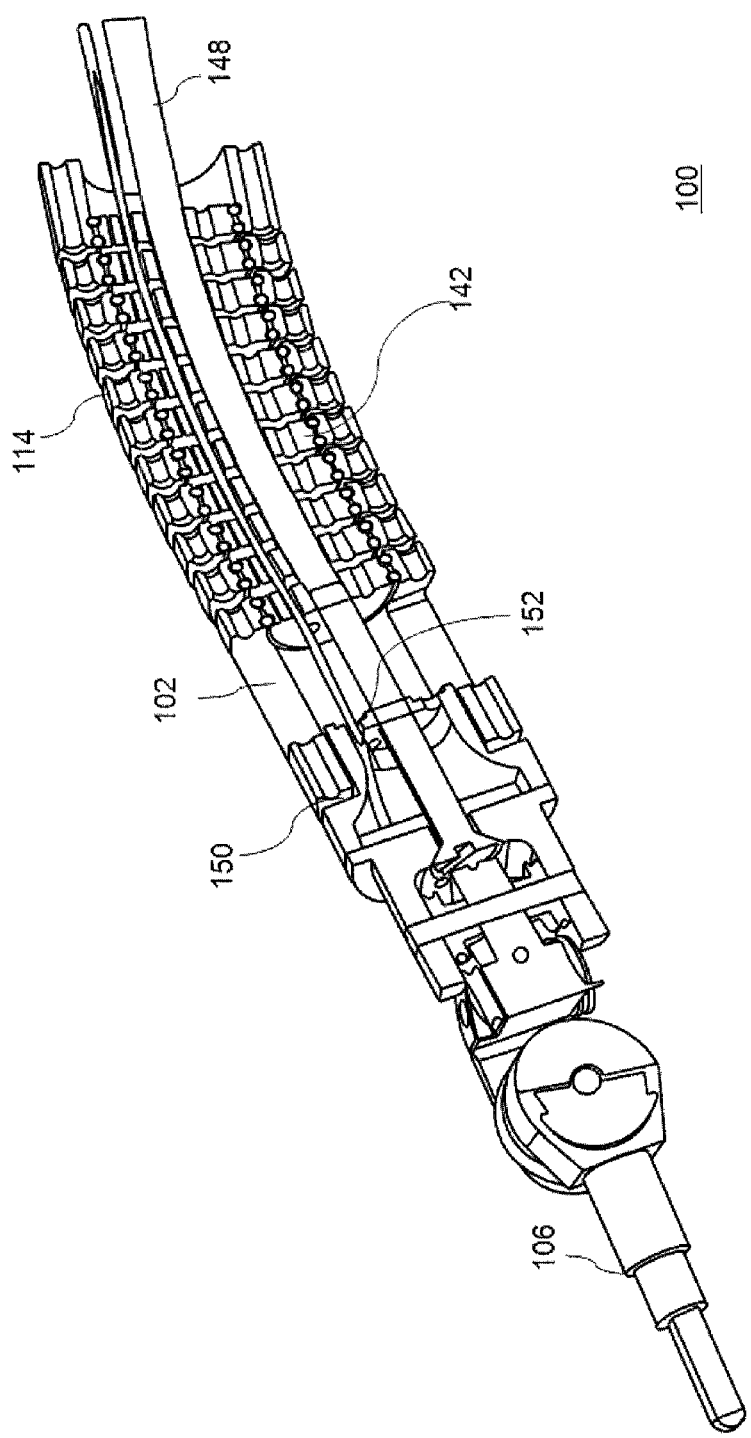
FIG. 4 illustrates a sectional view of the robotic system, in accordance with another embodiment of the present specification.

FIG. 4 illustrates the arrangement 100, in accordance with another embodiment. In this embodiment, the roll motion of the end effector 106 is achieved by using a flexible shaft, hereafter referred to as the roll spine 148, instead of roll cables. Further, in this embodiment, the end effector assembly 106 is secured to the articulation joint assembly 102 through a thrust bearing 150. The roll spine 148 is guided along the articulation joint assembly 102 through the plurality of disks, each similar to the disk 114, described above with reference to FIG. 3. As shown in FIG. 3, slot 140 in the core 142 of the disk 114 serves as the passage for the roll spine 148. In this embodiment, the core 142 of each of the plurality of disks and the roll spine 148 can rotate simultaneously about the longitudinal axis passing through the centre of the disks 114. The rotation of the roll spine 148 along with the disk cores 142 will in turn cause the roll motion of the end effector assembly 106. The simultaneous rotation of the core 142 inside each of the plurality of disks such as the disk 114 ensures that the end cable entry points 152 remain in line with the end effector assembly 106.

Figure 5:
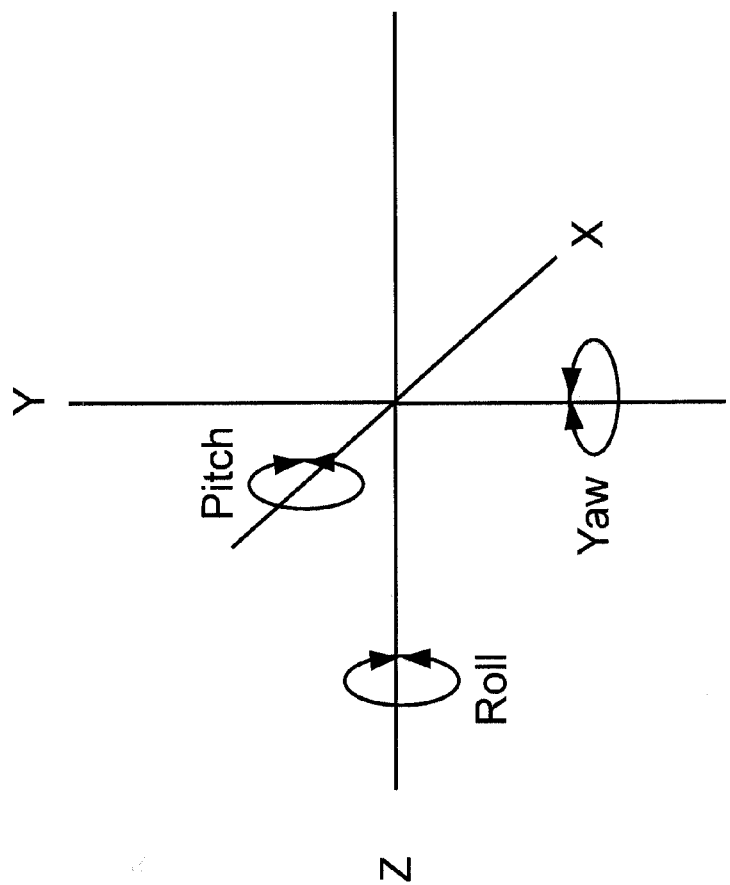
FIG. 5 illustrates the axes discussed herein and the pitch, roll and yaw associated with each.

The pitch and yaw motions can be achieved in substantially the same way as illustrated in the embodiment described above and shown in FIG. 1. Indeed, for greater clarity, FIG. 5 shows the pitch, yaw and roll motions contemplated herein with respective labels labeling the X, Y and Z axis.

Figure 6:
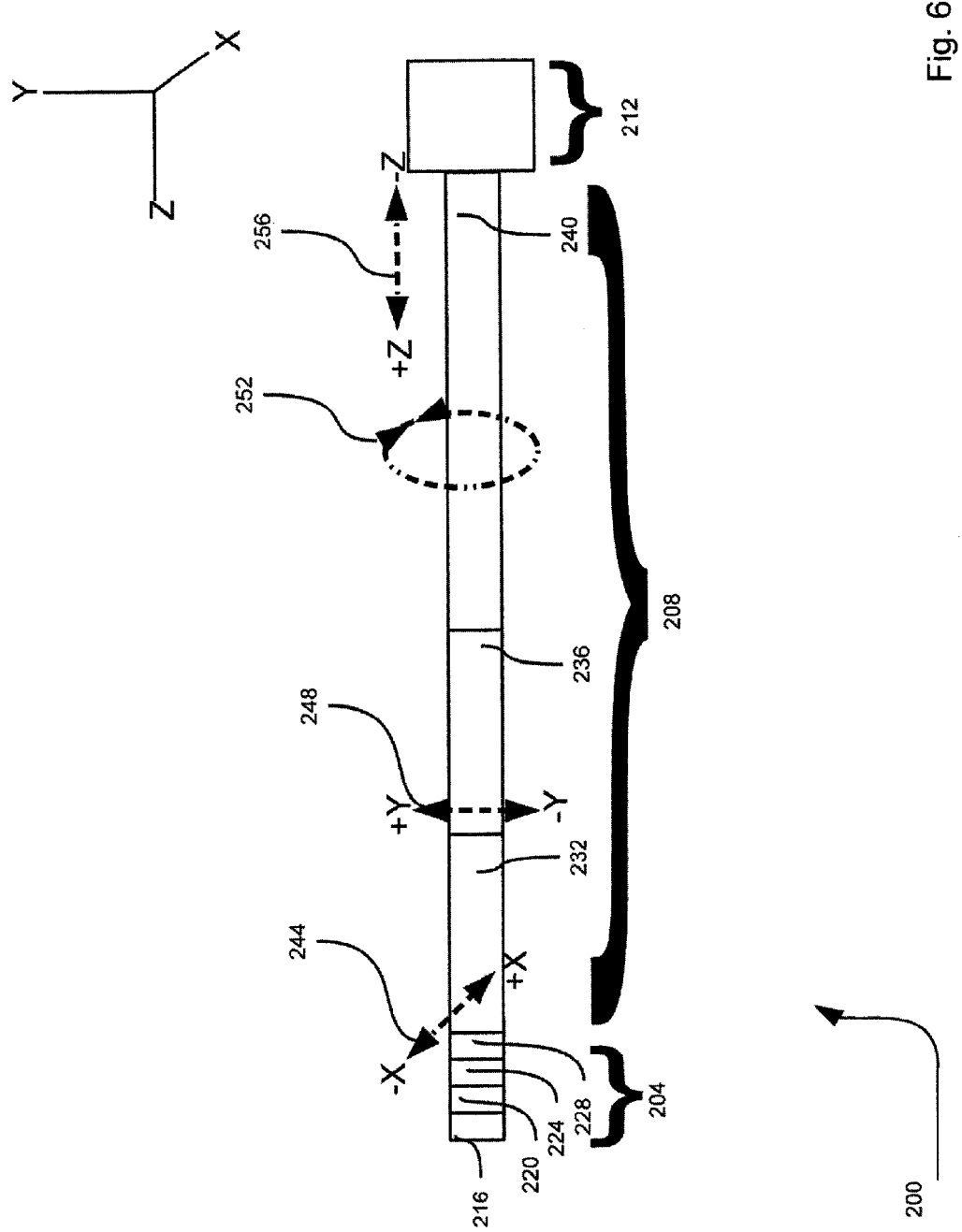
FIG. 6 illustrates a schematic representation of a robotic system in accordance with another embodiment.

Referring now to FIG. 6, a schematic representation of a robotic system is indicated generally at 200. System 200 comprises an end effector assembly 204, a coarse-movement assembly 208 and a control unit 212.

As shown in FIG. 6, robotic system 200 is not intended to show exact mechanical interactions but to provide a conceptual mechanical framework which can be implemented according to other teachings herein or variants thereon that will occur to those skilled in the art and who are familiar with this specification. As will become apparent from further reading, robotic system 200 is a variant on arrangement 100.

End effector assembly 204, can be implemented using any known or future conceived surgical end effector, and is generally analogous to end effector assembly 106. In a present illustrative embodiment, end effector assembly 204 comprises an end effector 216, and, optionally, one or more of a fine-X-axis effector 220 for pitch, a fine-Y-axis effector 224 for yaw, and a fine-Z-axis effector 228 for roll of the end effector 216. The end effector 216 can be, for example, a clamp, a spatula, surgical scissors or the like. End effector assembly 204 is thus configured for linear or rotating movement along one or more of the X axis, Y axis, or Z axis. In addition, end effector 216 can be used for a medical procedure once it is in position. In general, it is contemplated that end effector assembly 204 can be implemented so that end effector 216 with fine movements that include can include a pitch of about +/−ninety degrees from neutral; a yaw of about +/−ninety degrees from neutral; and a roll of about 270 degrees from neutral. Where end effector 216 is a pair of scissors (not the spatula cautery shown in FIGS. 1 and 4) the end effector 216 can include a jaw with an open and close range of between about zero and about sixty degrees.

Figure 7:
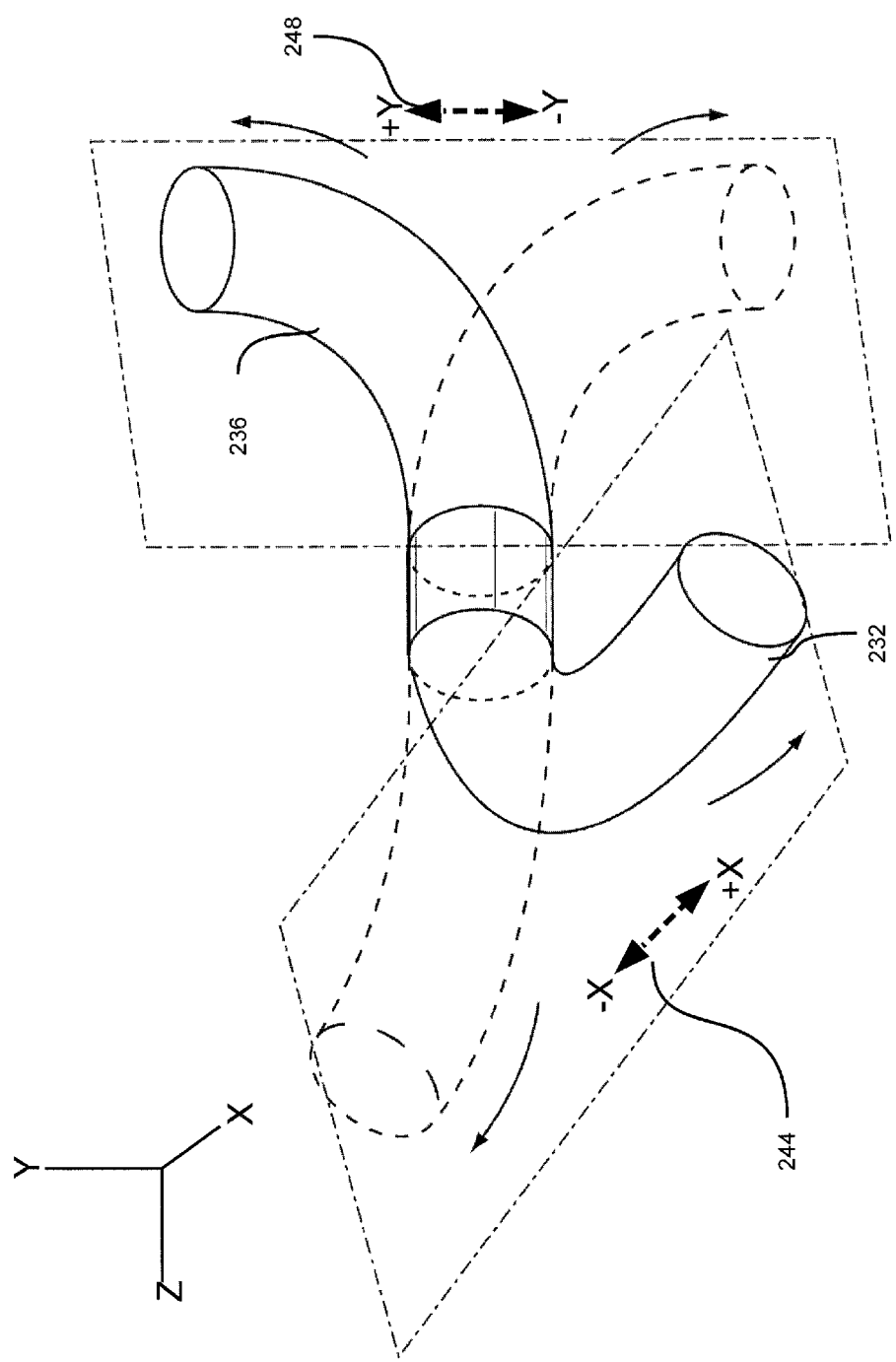
FIG. 7 illustrates certain elements of the robotic system of FIG. 6 in isolation from other elements to provide further illustration about those elements.
Figure 8:
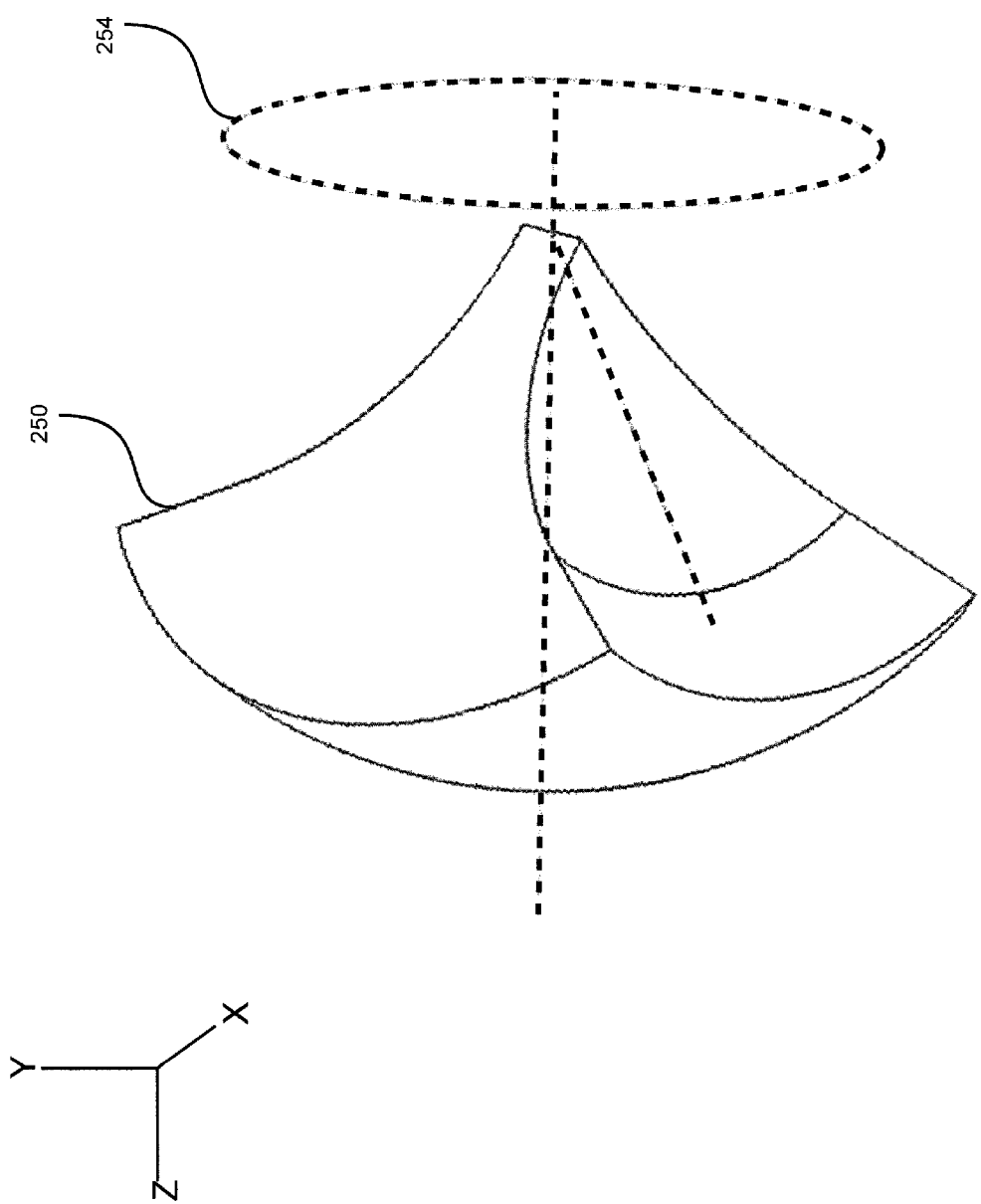
FIG. 8 illustrates a perspective view of a solid shape that represents the range of motion provided by the elements in FIG. 7.
Figure 9:
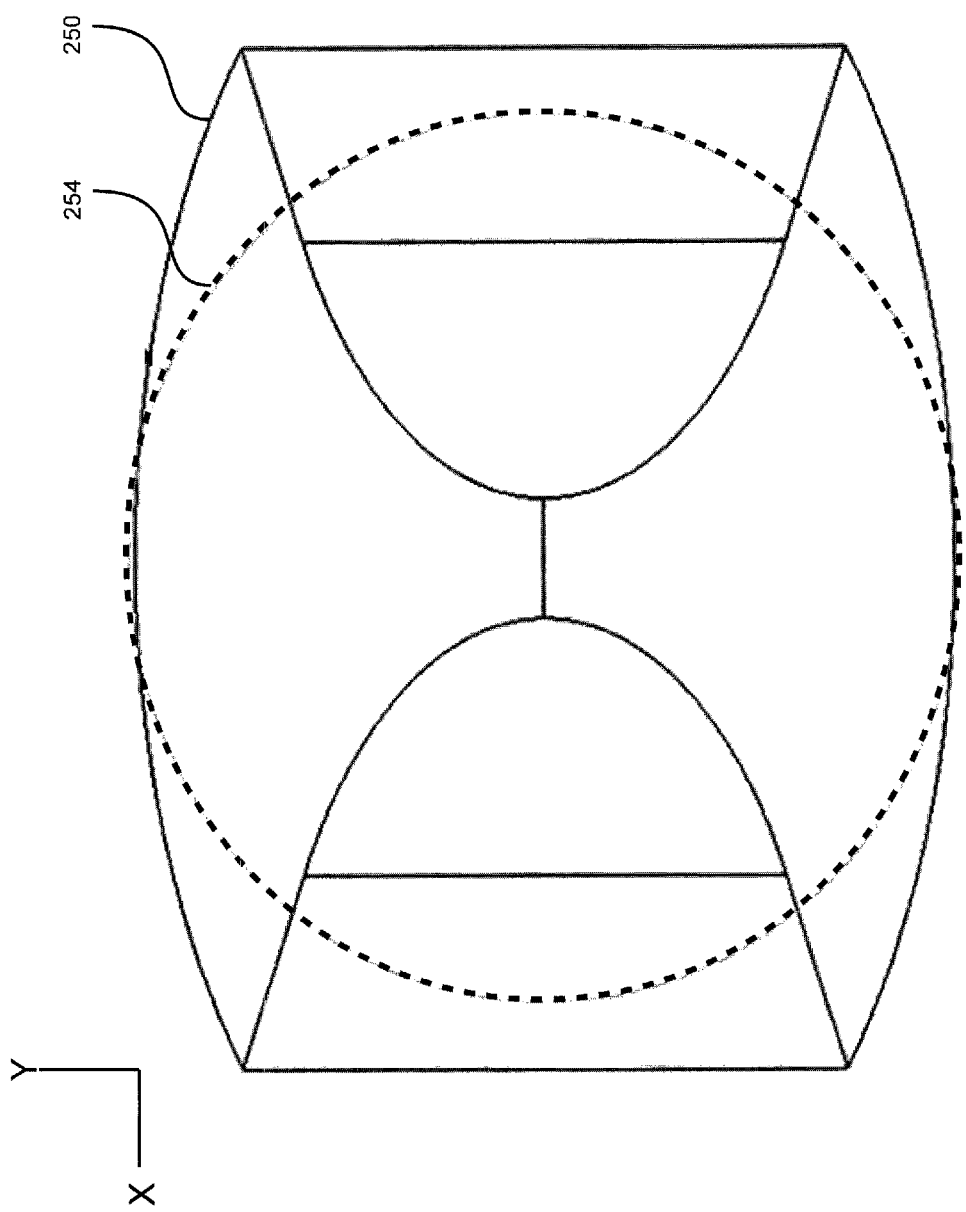
FIG. 9 illustrates a top view of the solid shape of FIG. 8 that represents the range of motion provided by the elements in FIG. 7.

Coarse-movement assembly 208 comprises an X axis assembly 232, a Y axis assembly 236, and a rotation assembly 240. The order in which X axis assembly 232, Y axis assembly 236, and rotation assembly 240 are provided can be modified from that shown, though the end effector assembly 204 is typically positioned on the distal tip of system 200. In variants, either the X axis assembly 232, or the Y axis assembly 236, or the rotation assembly 240, or any two of them, are omitted. The distal tip of X axis assembly 232 is configured for linear movement in the +X and −X direction, as labeled at XX-arrow 244. Expressed differently, the linear movement in the +X and −X direction provides wrist movement for the end effector assembly 204 in the +X and −X direction. The distal tip of Y axis assembly 236 is configured for linear movement in the +Y and −Y direction, as labeled at YY-arrow 248. Expressed differently, the linear movement in the +Y and −Y direction provides wrist movement for the end effector assembly 204 in the +Y and −Y direction. The contemplated movement in the +X and −X direction, and the movement in the +Y and −Y direction are shown in greater detail in FIG. 7, which shows X axis assembly 232 and Y axis assembly 236 in isolation from end effector assembly 204 and rotation assembly 240. FIG. 8 and FIG. 9 show a solid shape 250, the volume of which represents the range of motion that can be effected by X axis assembly 232 and Y axis assembly 236 shown in FIG. 7. Aperture 254 represents an example of an aperture window through which end effector assembly 204 can pass, while solid shape 250 shows that end effector 216 itself can reach locations that are beyond the perimeter of the aperture 254. Aperture 254 is thus illustrative of the fact that end effector 216 can be navigated through passageways without interfering with healthy tissue that lies outside the perimeter of aperture 254. For example, aperture 254 can represent the opening of the human mouth, which is itself smaller than the mouth itself. Thus it will now be apparent that one of the other applications of system 200 includes procedures that are performed in the mouth or in the throat.

Referring again to FIG. 6, all or a portion of rotation assembly 240 is configured for roll, (i.e. rotational movement around the Z axis), as labeled at arrow 252. Macro linear movement along the Z axis, as labeled at ZZ-arrow 256, can be effected using a Z axis controller, not shown, which extends or retracts robotic system 200 along the Z axis. In general it will be understood that the figures and the description do not show another set of controls that guide the entirety of system 200 generally towards a target area, and that system 200 is used to deftly maneuver end effector 216 to that target area.

Control unit 212 houses control mechanisms, such as, for example, servo motors for actuating cabling or rods originating in control unit 212 and travelling within the remainder of system 200 to implement the various possible movements offered by system 200. Control unit 212 can be active or passive. In an active configuration, control unit 212 comprises a self contained unit with servo motors. In a passive configuration, control unit 212 is driven from an external power source. An electronic control module, not shown, connects to the various servo motors to provide control signals to system 200, responsive to instructions from an operator.

Figure 10:
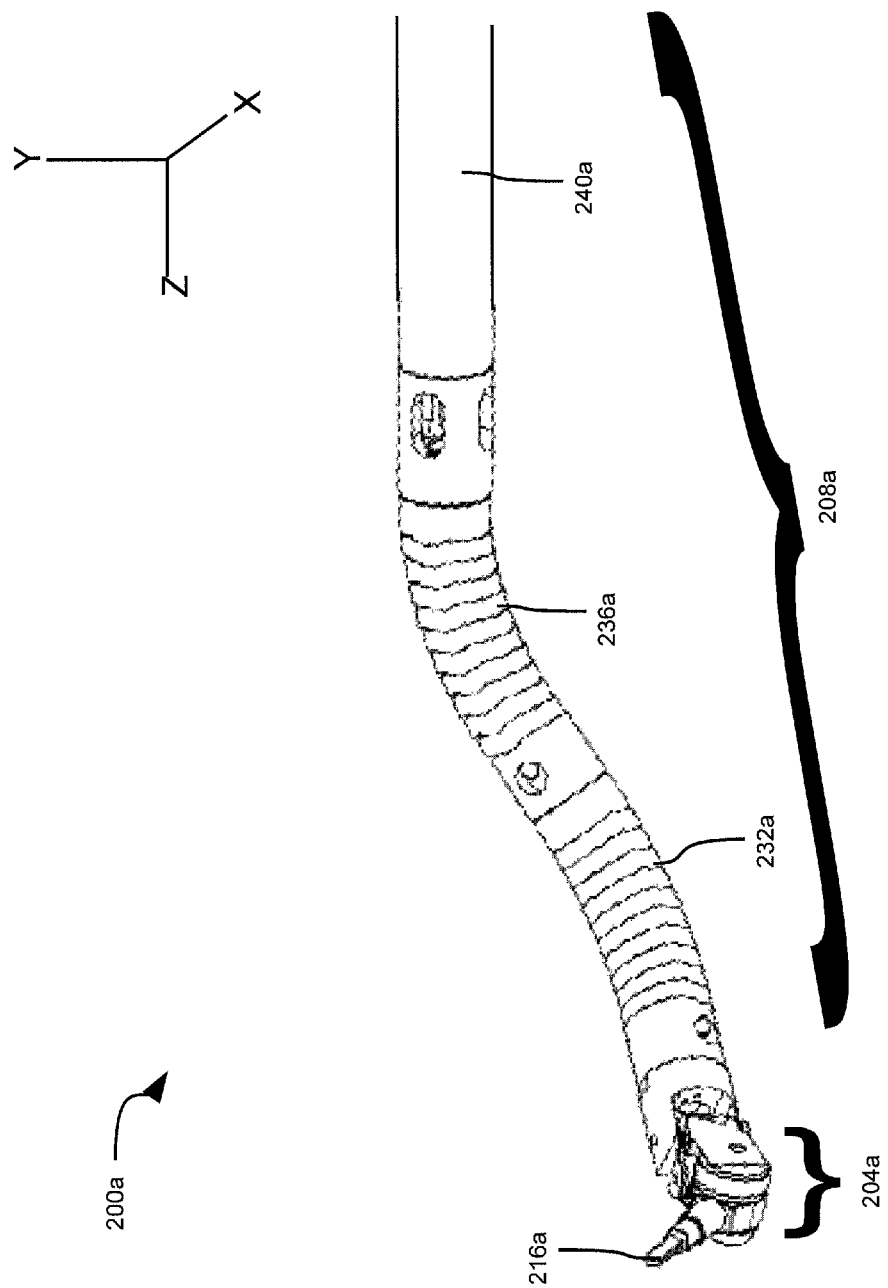
FIG. 10 illustrates an example implementation of the robotic system of FIG. 6 in accordance with another embodiment.
Figure 11:
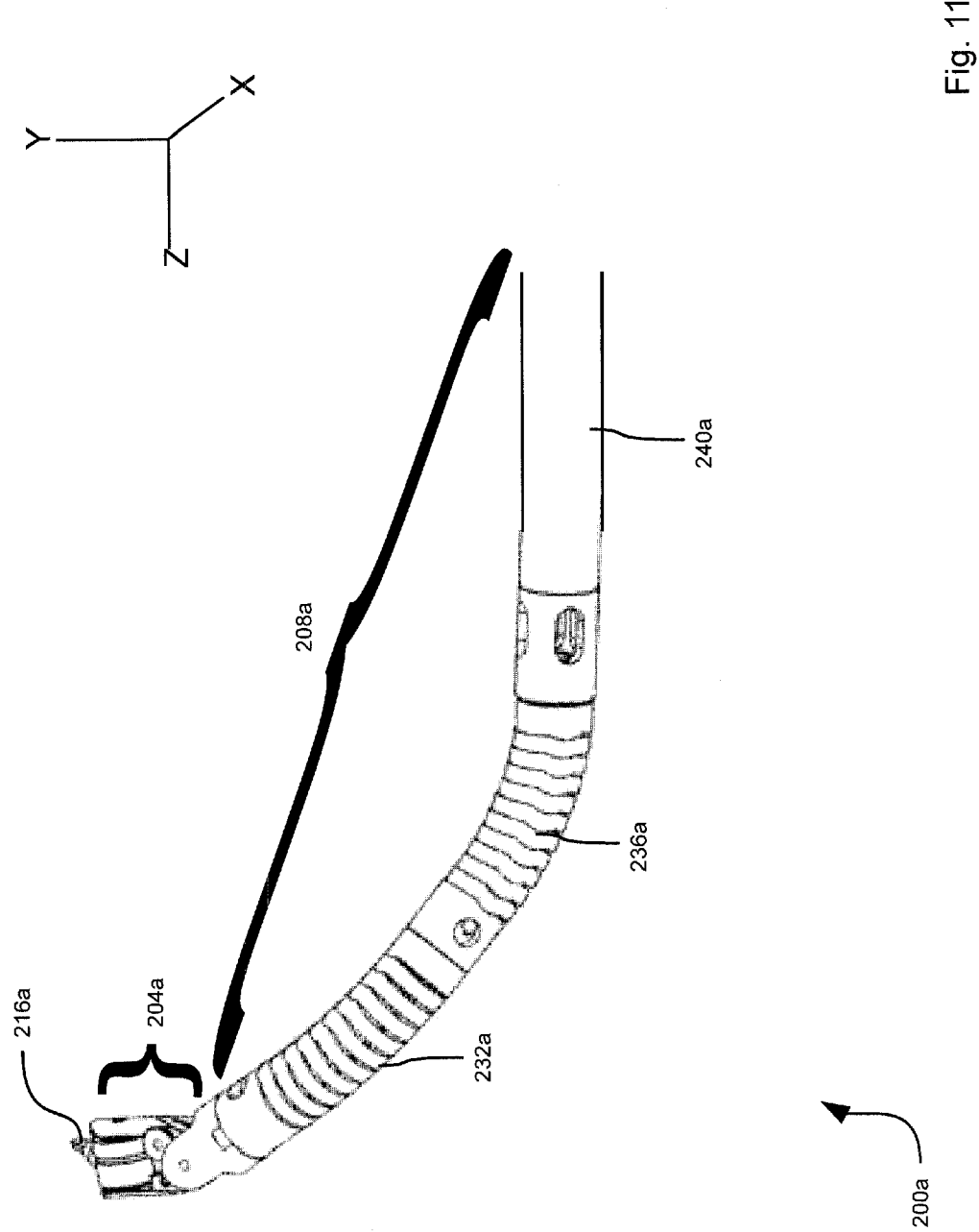
FIG. 11 illustrates an example implementation of FIG. 10 in another position.

Referring now to FIG. 10 and FIG. 11, a non-limiting example implementation of robotic system 200 is shown as robotic system 200a. Robotic system 200a is based on the components of schematic robotic systems 200 and therefore like elements bear like references except followed by the suffix "a". FIG. 10 shows robotic system 200a in a first position while FIG. 11 shows robotic system 200a in a second position. However, it will now be understood from the foregoing that robotic system 200a can be placed in a large number of different positions, other than that shown, based on the teachings herein.

Of note is that end effector assembly 204a comprises a spatula cautery for its end effector 216a, which can be used for urging or pushing an article of tissue in a particular direction, or cutting tissue by electrical means, but it should be understood that other types of medical instruments are contemplated and indeed different end effector assemblies, other than that shown, can be used with robotic system 200a or its variants.

Also of note is that X-axis assembly 232a is based on articulating joint assembly 102 (and its plurality of disks 114) as described in relation to arrangement 100. By the same token, Y-axis assembly 236a is also based on articulating joint assembly 102 (and its plurality of disks 114), however Y-axis assembly 236a is disposed ninety degrees in relation to X-axis assembly 232a. In this manner, articulating joint assembly 102 as it is used to implement X-axis assembly 232a provides X-axis movement as discussed above, while articulating joint assembly 102 as it is used to implement Y-axis assembly 236a provides Y-axis movement as discussed above.

Figure 12:
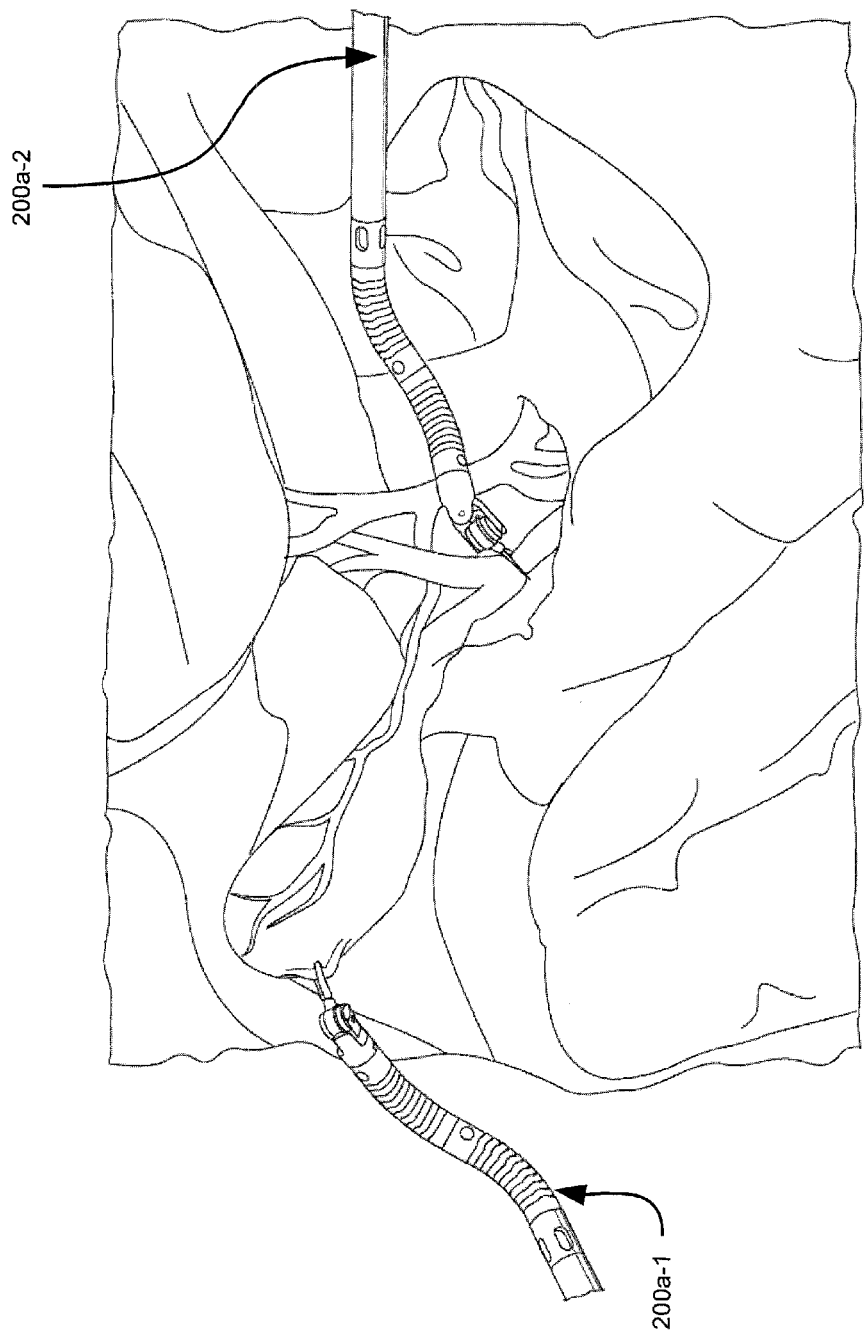
FIG. 12 illustrates the robotic system in the context of an example surgical procedure.

Referring now to FIG. 12, a first instance of robotic system 200a, bearing reference 200a-1, and a second instance of robotic system 200a, bearing reference 200a-2, are shown in situ, proximal to a gall bladder of a patient and for use as part of a surgical procedure to remove the gall bladder. Robotic system 200a-1 is shown with a clamp-type end effector for holding the gall bladder, while robotic system 200a-2 is shown with a surgical scissor type end effector for severing the gall bladder. It is to be understood that FIG. 12 is a non-limiting example of a surgical procedure that can be performed using the present specification. For instance in variations, gall bladder removal may be effected without using two robotic systems 200a, but instead using another type of instrument to effect either the clamping or cutting function. Furthermore, other types of surgical procedures are contemplated. However, FIG. 12 is illustrative of: a) the limited space which can accommodate robotic system 200a in the performance of the procedure; and b) the fact that the range of mobility of robotic system 200a, and its variants, can provide excellent access to the surgical target area while also minimizing or reducing the risk of inadvertently damaging or traumatizing healthy surrounding tissue, as end effector assembly 204a can be navigated to the target area while avoiding, minimizing or reducing contact with the healthy surrounding tissue.

Referring back to FIGS. 9 and 10, those skilled in the art will now appreciate that the Y-axis movement provided by Y-axis assembly 236a, the X-axis movement provided by X-axis assembly 232a, and the coarse-rotational movement provided by Z-axis assembly 240a. In one implementation, the Z-axis assembly 240a is configured to rotate (i.e. provide roll) plus or minus ninety degrees, independent from the roll provided by fine-Z-axis effector 228 (as shown in FIG. 6). When combined with the movement offered by the X-axis assembly 232a and the Y-axis assembly 236a, the skilled reader will now appreciate that a coarse-movement assembly 208a can position end effector assembly 204a anywhere within a virtual cone (as shown in FIGS. 8 and 9) that is defined by the range of movement of coarse-movement assembly 208a, but again such positioning of end effector assembly 204a can be done deftly so as to avoid, reduce or minimize contact with healthy surrounding tissue that is within the path towards the target surgical area.

While embodiments have been illustrated and described, it will now be clear that the specification is not limited to these embodiments. Numerous modifications, changes, variations, substitutions and equivalents will now be apparent to those skilled in the art without departing from the spirit and scope of the specification. For example, X-axis assembly 232a and Y-axis assembly 236a are each shown with ten disks comprised of disks like disk 114, which each provide about up to about sixty degrees of flexion. However it is contemplated that X-axis assembly 232a and Y-axis assembly 236a could have a different number of disks, such as between about five and about fifteen disks, according to the desired range of flexion.

Furthermore, it should be understood that the material chosen for disk 114 and its variants is not particularly limited, but presently contemplated materials include stainless steel such as stainless steel 316L families, or titanium such as titanium Ti-6Al-4V families.

Furthermore, it should be understood that the configuration of cabling shown in FIG. 1 and FIG. 4 is a non-limiting example. Indeed in other configurations such as a rigid but flexible rod is contemplated that can push and pull one the degrees of freedom so only one rod is used in place of a pair of cables that are able to pull in opposite directions. In another configuration, where system 200a has six degrees of freedom (four for the end effector assembly 204a, (roll, pitch, yaw, jaw open/close) and two for the coarse-movement assembly 208a (pitch/yaw), each degree of freedom can have a set of two cables that works independently from the others, e.g. actuating the shaft pitch shall not actuate the end effector pitch. Also it can be noted that end effector 216 yaw could be combined with a jaw open/close where end effector 216 is a pair of surgical scissors or a clamp.

Figure 13:
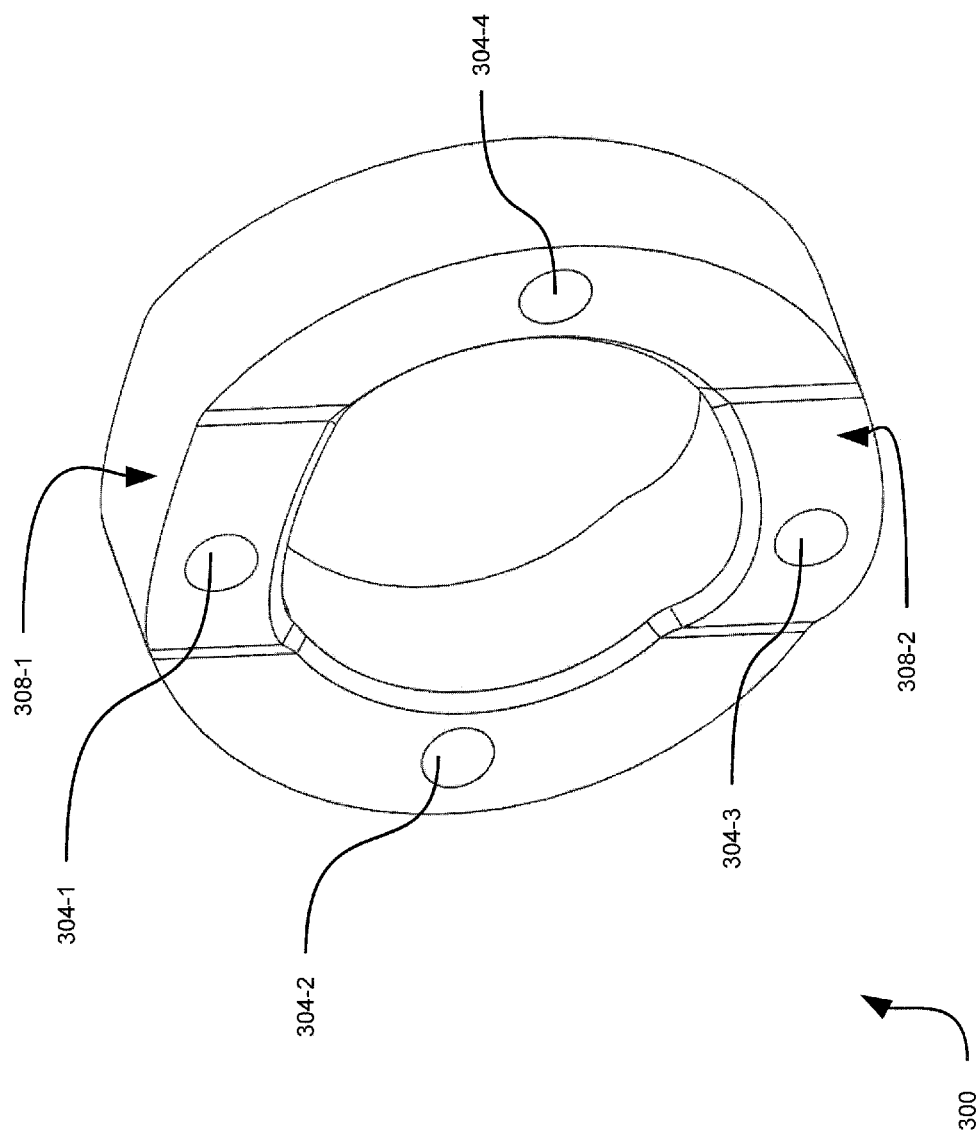
FIG. 13 illustrates a perspective view of an another embodiment for a ring of a disk element.
Figure 14:
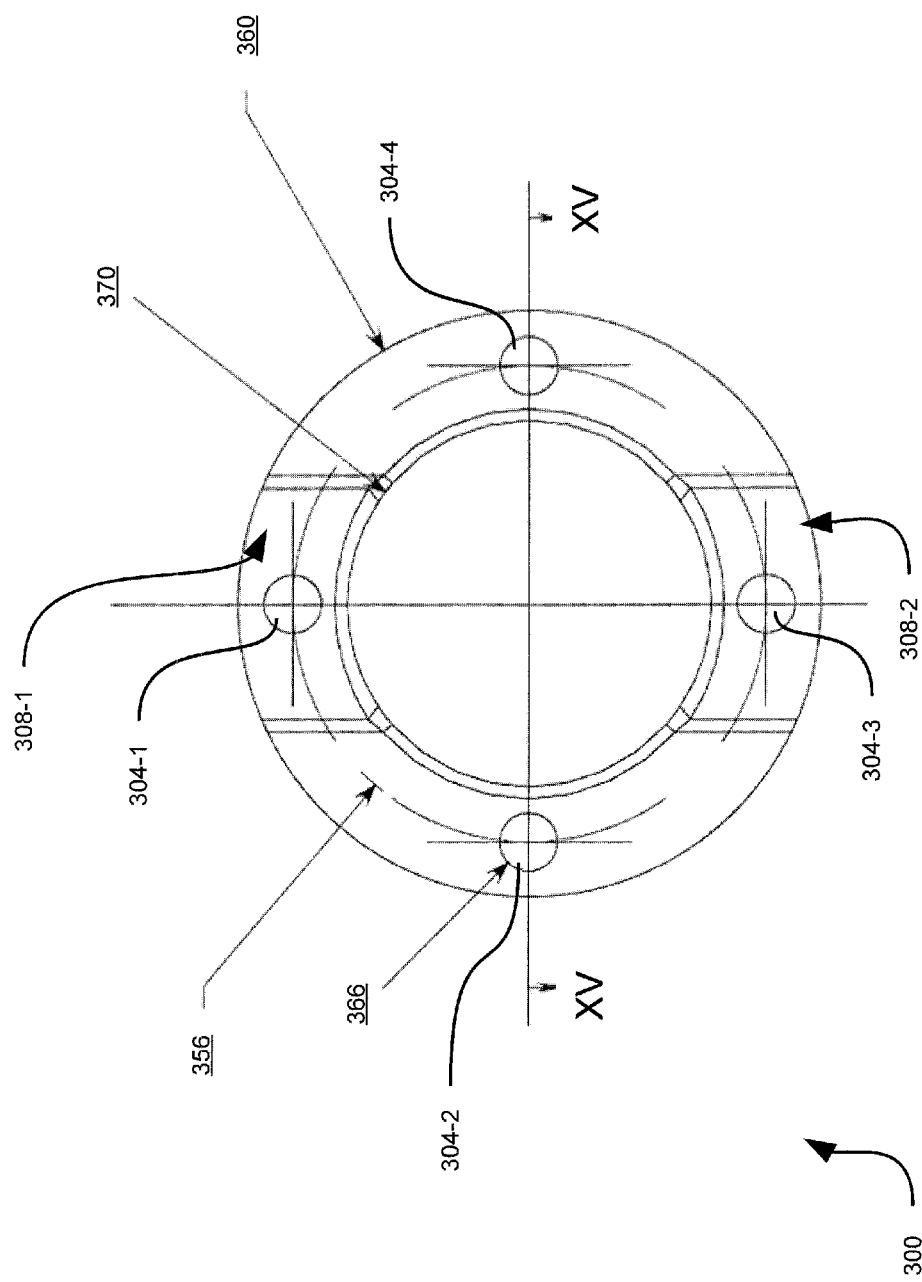
FIG. 14 illustrates a front view of the ring of FIG. 13.
Figure 15:
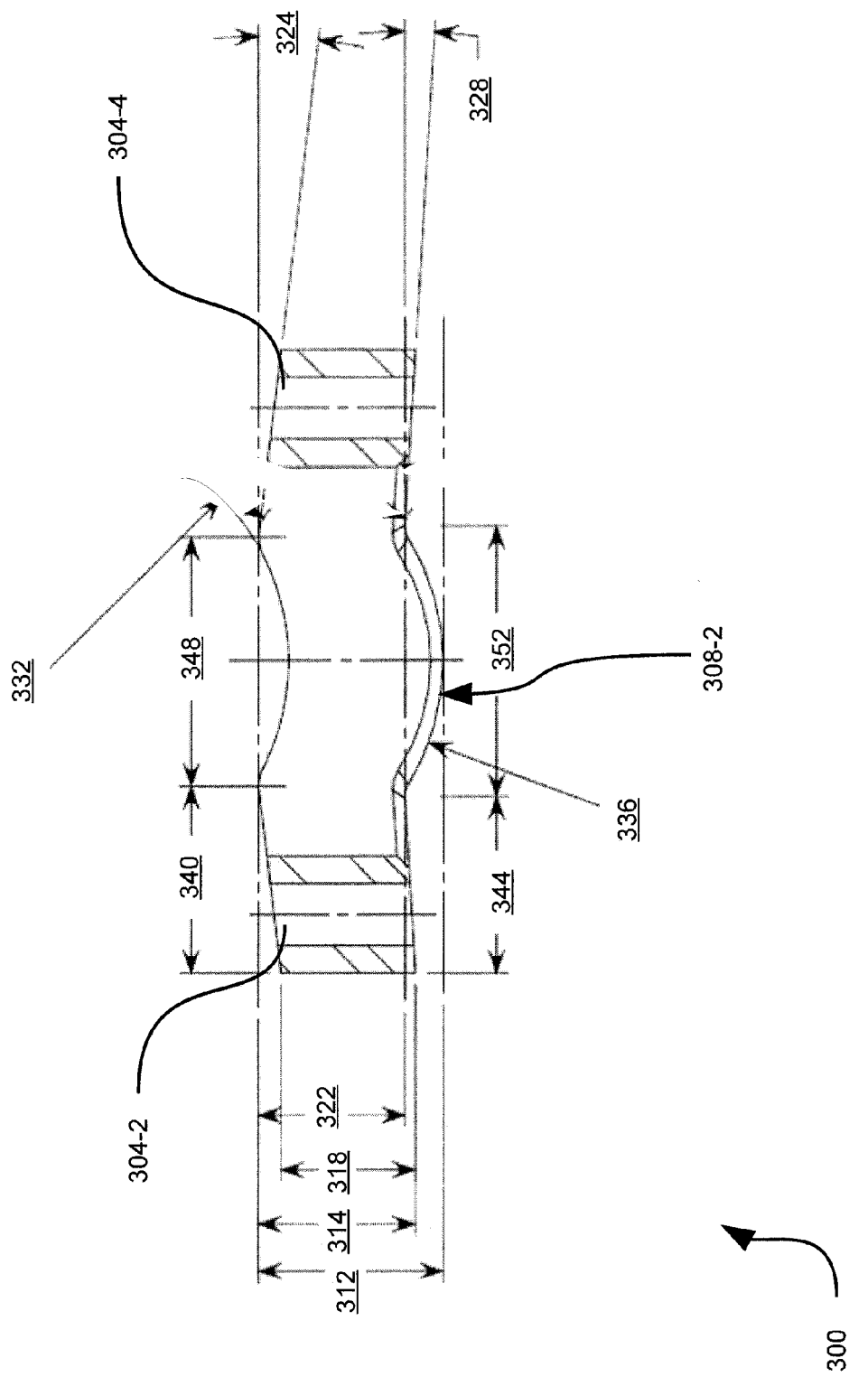
FIG. 15 illustrates a sectional view of the ring of FIG. 14.

Furthermore, it should be understood that the configuration of disk 114 as shown in FIG. 2 and FIG. 3 is a non limiting example. Indeed, FIG. 13, FIG. 14 and FIG. 15 show different views of a ring 300 in accordance with another embodiment that can be used as the outer portion of disk 114 and omitting central part 142. While ring 300 does not show a central part 142 as shown in relation to disk 114, central part 142 can also be included with ring 300, or a variant on central part 142 can be provided. Understanding of ring 300 and disk 114 from this specification will leave a person of skill in the art with an appreciation of further variants.

Referring still to FIGS. 13, 14 and 15, ring 300 comprises a plurality of slots 304-1, 304-2, 304-3 and 304-4 which are collectively referred to herein as slots 304 and generically as slot 304. (This nomenclature is used elsewhere). Slots 304 are configured, as will be discussed further below, to allow passage of cabling therethrough. In variants, fewer or greater slots can be provided depending on the desired number of control cables or rods. It has been noted that when X axis assembly 232a or Y axis assembly 236a are in a bent configuration, there is a resulting misalignment of slots 304 between respective rings 300. This misalignment can cause additional tension and shear in the cable. In a present embodiment, slots 304 are thus provided with a diameter and depth to mitigate or obviate this effect. Slots 304 are thus provided with a diameter larger than the diameter of the cable but also with a depth so that cable is not subject to shear when slots 304 are misaligned between respective rings 300, thereby providing enough freedom to the cable to move inside the rings in the most bent configuration. In a presently preferred configuration, for example, the diameter of each slot 304 is about twenty-five percent larger than the diameter than the cable to be passed therethrough.

When viewed from the perspective in FIG. 15, each ring 300 appears as an arc. However, as also seen in FIG. 13 and FIG. 14 each ring 300 also comprises a first curved section 308-1 and a second curved section 308-2. As best seen in FIG. 15, the curvature of each curved section 308 has a radius opposite to the arc. The arc permits the type of bending of system 200a as contemplated in FIG. 7, FIG. 10 or FIG. 11, while the curved sections maintain alignment and directionality of such bending.

Table I provides a list of dimensions of the non-limiting example of ring 300 as well as non-limiting examples of dimensions for those elements.

TABLE I

| Dimension Description | Reference | Example Dimension (All dimensions can be read as being "about" the number specified) | Unit | Comment (If any) |
|---|---|---|---|---|
| Overall Thickness | 312 | 2.39 | mm | |
| Thickness omitting convex portion of curved section 308 | 314 | 2 | mm | |
| Overall interior Thickness (omitting arc and curved section 308) | 318 | 1.74 | mm | |
| Thickness omitting concave portion of arc | 322 | 1.89 | mm | |
| Angle defining convex portion of arc | 324 | 7 | Degrees | |
| Angle defining concave portion of arc | 328 | 3.5 | Degrees | Geometrically this dimension can be about half of the dimension of 324 to provide a symmetrical stop |
| Concave radius of curved section 308 | 332 | 3.00 + .003/−0.00 | mm | |
| Concave radius of curved section 308 | 336 | 3.00 + .003/−0.00 | mm | |
| Length from ring periphery to concave portion of curved section 308 | 340 | 2.4 | mm | |
| Length from ring periphery to convex portion of curved section 308 | 344 | 2.27 | mm | |
| Length of sector across concave portion of curved section 308 | 348 | 3.2 | mm | |
| Length of sector across convex portion of curved section 308 | 352 | 3.47 | mm | |
| Center line of each slot 304 in relation to diameter of ring 300 | 356 | 6.5 | mm | |
| Outer Diameter of ring 300 | 360 | 8 | mm | |
| Diameter of each slot 304 | 366 | 0.8 | mm | [0.031 Thru] |
| Inner diameter of ring 300 | 370 | 5 | mm | +0.04 +0.02 Thru |

The present specification offer one or more advantages. For example, the present specification provides a robotic system for use in MIS that allows for imparting the roll motion to the end effectors without the need of rotating the entire robotic arm, thus providing movement of end effectors that can be independent of the robotic arm. Thereby, unintended contact with healthy tissues and organs by the surgical instrument can be mitigated or avoided.

The invention claimed is:

1. A robotic surgical system comprising:
an end-effector assembly comprising a surgical instrument configured for fine-movement responsive to a first control mechanism in order to perform a medical procedure at a target area using said surgical instrument; and
a coarse-movement assembly connected to said end-effector assembly, said coarse-movement assembly configured for coarse-movement responsive to a second control mechanism in order to position said end-effector assembly near said target area, said coarse-movement comprising at least a wrist movement for said end-effector assembly, said first control mechanism and said second control mechanism being independently controllable from each other,
said coarse-movement assembly comprising:
a first articulating joint assembly having a longitudinal axis and movable within a first plane, said first articulating joint assembly including a first series of connected disks, each disk being independently moveable within said first plane; and
a second articulating joint assembly having a longitudinal axis and movable within a second plane perpendicular to said first plane, said second articulating joint assembly including a second series of connected disks, each disk being independently moveable within said second plane,
at least one cavity extending longitudinally along said first and second articulating joint assemblies, and at least one control cable implementing said first control mechanism and extending through said at least one cavity;
an opening separate from said at least one cavity extending longitudinally along said first and second articulating joint assemblies, and a flexible shaft coupled to said end-effector assembly and extending through said opening, wherein said flexible shaft is rotatable within said opening to impart a roll on said end-effector assembly and wherein rotation of the said flexible shaft is independent of any longitudinal movement of said flexible shaft; wherein each connected disk of said first and second series of connected disks further includes a freely rotatable core, said cavity and said opening being located in said core and wherein each of said core and said flexible shaft is rotatable simultaneously and independently about respective said longitudinal axes.

2. The robotic surgical system of claim 1 wherein said surgical instrument comprises at least one of a clamp, a spatula, and surgical scissors.

3. The robotic surgical system of claim 1 wherein said flexible shaft is coupled to said end-effector assembly by a thrust bearing.

4. The robotic surgical system of claim 1 wherein the longitudinal axis of said first articulating joint assembly is disposed at about ninety degrees relative to the longitudinal axis of said second articulating joint assembly.

5. The robotic surgical system of claim 1 wherein said first and second series of connected disks are each comprised of about 10 disks and wherein each of said first and second series of connected disks provides up to about 60° of flexion.

6. The robotic surgical system of claim 1 wherein said first and second series of connected disks are comprised of stainless steel.

7. The robotic surgical system of claim 1 wherein said first and second series of connected disks are comprised of titanium.

\* \* \* \* \*